US008738146B2

(12) United States Patent
Guiraud et al.

(10) Patent No.: US 8,738,146 B2
(45) Date of Patent: May 27, 2014

(54) CONTROL DEVICE FOR SELECTIVE ACTIVATION OF ELECTRODE CONFIGURATION

(75) Inventors: David Guiraud, Montpellier (FR); David Andreu, Montarnaud (FR); Guy Charvin, Antibes (FR); Jean-Louis Divoux, Cagnes sur Mer (FR)

(73) Assignees: Inria Institut National de Recherche en Informatique et en Automatique, Le Chesnay (FR); Obelia, Montpellier Cedex 5 (FR); Centre National de la Recherche Scientifique (C.N.R.S), Paris (FR)

( * ) Notice: Subject to any disclaimer, the term of this patent is extended or adjusted under 35 U.S.C. 154(b) by 0 days.

(21) Appl. No.: 13/641,366

(22) PCT Filed: Apr. 15, 2011

(86) PCT No.: PCT/FR2011/050869
§ 371 (c)(1),
(2), (4) Date: Dec. 13, 2012

(87) PCT Pub. No.: WO2011/128601
PCT Pub. Date: Oct. 20, 2011

(65) Prior Publication Data
US 2013/0110200 A1 May 2, 2013

(30) Foreign Application Priority Data
Apr. 16, 2010 (FR) .................................... 10 01625

(51) Int. Cl.
*A61N 1/36* (2006.01)

(52) U.S. Cl.
USPC ........................................................ 607/59

(58) Field of Classification Search
USPC ........................................................ 607/59
See application file for complete search history.

(56) References Cited

U.S. PATENT DOCUMENTS

| 6,208,894 | B1* | 3/2001 | Schulman et al. ................. 607/2 |
| 2003/0056135 | A1 | 3/2003 | Splett et al. |
| 2003/0139783 | A1 | 7/2003 | Kilgore et al. |
| 2004/0172083 | A1 | 9/2004 | Penner |
| 2005/0085864 | A1 | 4/2005 | Schulman et al. |

* cited by examiner

*Primary Examiner* — George Manuel
(74) *Attorney, Agent, or Firm* — Davidson, Davidson & Kappel, LLC

(57) ABSTRACT

A control device implantable in a human body—includes a control unit and at least one electrode, said control unit being connected to each electrode to control stimulation and/or measurement thereof. The control unit includes: a timing clock; a memory storing configuration data defined to enable configuration of each electrode correlated with identifiers; a memory storing program data describing a time profile correlated with identifiers; an executor activatable to send each electrode electric pulses corresponding to a predetermined program according to a predetermined electrode configuration, according to the clock; a sequencer arranged to receive an ordered plurality of pairs, each including an electrode configuration identifier and a program identifier, and selectively to activate the executor with the electrode and program configuration pairs denoted by the pairs of identifiers received as an input, according to the order thereof and the clock.

10 Claims, 3 Drawing Sheets

CONTROL DEVICE FOR SELECTIVE ACTIVATION OF ELECTRODE CONFIGURATION

The invention relates to the control of the human body and more particularly to stimulation and/or measurement of physiological quantities on sites of the sensory-motor system of the human body, with the purpose of overcoming the sensory-motor deficiencies following an accident, or subsequent to a disease.

BACKGROUND

The application finds a particular implementation in neural stimulation, and more particularly in stimulation of the peripheral nervous system. However, it may perfectly be applied to other types of stimulation, such as surface stimulation, epimysial stimulation, or functional electric stimulation applied to the brain and/or to the spinal cord.

The stimulation or the measurement may be carried out on any physiological structure capable of generating an electric signal or reacting to the latter, most often in the form of an action potential.

Thus, axons grouped in bundles and then in nerves, the neurons themselves located in the brain or the spinal cord, the cardiac, skeletal muscle fibres or those of certain smooth muscles, sensorial organs, are as many structures which may either be observed or stimulated.

Finally, although the presented technology is firstly interested in implanted systems, the concept would be identical for external or mixed systems.

Many accidents and diseases may leave a human being without any control of his/her body, or only with partial control, because of an alteration or degradation of the nervous system.

These affections may attain motor functions, such as mobility of the upper or lower portion of the body, or non-motor functions such as urination.

In these situations, the affected persons not only suffer from the direct consequences of the induced deficiencies, but also from major secondary effects such as scars, osteoporosis, or the need of being catheterized in order to urinate.

In order to respond to this situation, physicians and scientists have been studying the human nervous system for many years. Some research work aims at regenerating it and other research work at compensating its deficiency by artificial control.

SUMMARY OF THE INVENTION

The invention relates to this second type of research work, and allows restoration or modulation of certain motor, sensorial or organic activities of the human body by means of a device and system for neural stimulation which will compensate for or retrain the defective control of the nervous system.

Certain results have been able to be obtained by research work in this field. Several devices from the industrial world and from the academic world have thus been proposed.

These devices rely on one or several electrodes implanted in the human body, which may be controlled in order to apply or measure an electric current or voltage at a nerve or a target structure, as mentioned above.

These devices have many drawbacks and are not yet capable of providing a real solution to the problem of the loss of motor ability, sensoriality, or control.

Indeed, they generally remain at an extremely local level, i.e. these devices are not able to communicate with each other, from the moment that this is not a single device centralizing all the electrodes and their control.

This means that the coordinated stimulation and/or measurement of a set of neural or muscular activities by a set of devices is not possible.

And therefore performing a complex and accurate function such as a deambulatory movement for example, is even less possible.

Certain solutions have proposed to have the devices communicate with each other. Nevertheless, the solutions have remained at a prototype stage or have never experienced any real application within the scope of complex functions.

Indeed, these solutions are either based on extracorporeal means for synchronizing implanted devices, or on centralization of the whole of the activities.

As regards the first solutions, the synchronization of implants, via extracorporeal devices, involves antenna constraints ensuring sufficient inductive coverage. These constraints prevent meeting the time accuracy requirements of less than 1 millisecond for practical application of human functions.

As regards the second solutions, the centralization of the whole of the activities of implants has the drawback of inducing major surgery. Indeed, this type of solution is not an evolutionary one, in the sense of the capability of supporting incremental implantation of implantable devices, for compensation of subsequent deficiencies, for example.

In fact, none of the solutions described to this day allow the application of several functions, or the management of possible interactions, interlacings and constraints between two functions. This limitation is seen both when the implants are independent and when they are not so, and both when the relevant nerves and/or muscles are different and when they are identical.

The invention improves the situation.

It is an object of the present invention to provide an implantable control device in a human body, comprising a control unit and at least one electrode. The control unit is connected to said or each electrode in order to control it in stimulation and/or in measurement.

The present invention provides a-control unit comprising
a timing clock,
a memory storing configuration data defined in order to allow the configuration of said or each electrode in correspondence with identifiers,
a memory storing program data describing a time profile in correspondence with identifiers,
an executor activatable in order to send to said or each electrode, electric pulses corresponding to a given program according to a given electrode configuration, as a function of the clock,
a sequencer laid out for receiving an ordered plurality of pairs each comprising an electrode configuration identifier and a program identifier, and for selectively activating the executor with the electrode configuration and program pairs designated by the pairs of identifiers received at the input, as a function of their order and to the clock.

The invention also relates to an implantable control system in a human body comprising a drive and at least one device as described above, connected in a wired network of the bus type, wherein the drive is laid out for sending said plurality of identifier pairs to the sequencer of said device.

BRIEF DESCRIPTION OF THE DRAWINGS

Other features and advantages of the invention will become better apparent upon reading the description which follows, drawn from examples given as an illustration and not as a limitation, drawn from drawings wherein.

DETAILED DESCRIPTION

The drawings and the description hereafter essentially contain absolutely certain elements. Therefore, they may not only be used for making the present invention better understood, but also for contributing to its definition, if necessary.

The present description is of a nature involving elements which may be protected by author rights and/or copyright. The owner of the rights does not object to identical reproduction by anyone of the present patent document or of its description, as it appears in the official files. For the remainder, his/her rights are entirely reserved.

Further, the detailed description is extended with the appendix A, which gives the formulation of certain implemented controls within the scope of the invention. This appendix is set apart for the sake of clarification and for facilitating back references. It is an integral part of the description, and may therefore not only be used for better understanding the present invention but also for contributing to its definition, if necessary.

Figure 1:
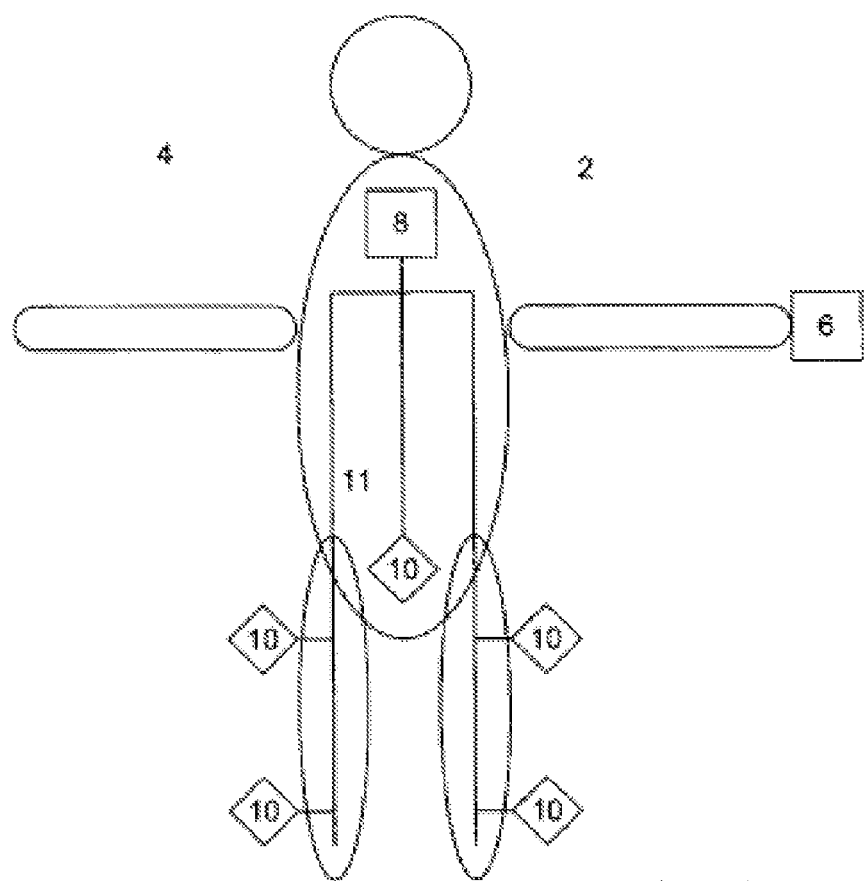
FIG. 1 illustrates a diagram of a system for controlling the human body according to the invention, implanted in a human body.

FIG. 1 illustrates a diagram of a neural stimulation system 2 implanted in a human body 4.

The neural stimulation 2 comprises an external control 6, a drive 8, and neural stimulation devices 10.

In the example described here, the external control 6 and the drive 8 communicate through a wireless signal, of the inductive link type or of the radio frequency (RF) communications link type.

Thus, the practitioner or the patient in the body 4 of whom the system for controlling the human body 2 is implanted, may control the motor functions/gestures which he/she desires to perform by means of a simple interface.

In the example described here, the drive 8 is implanted in the upper portion of the body 4. For example, it may be housed at a collar bone or at the abdomen of the body 4. It may be housed elsewhere, as one skilled in the art will be able to appreciate.

In the example described here, a device 10 is located at the bladder, and two devices 10 are positioned in each of the left and right legs, respectively.

The drive 8 is connected to the various neural stimulation devices 10 by means of a bus 11. The bus 11 is a set of conducting wires (for example a cardiac approved 2-wire cable IS-1), which transport both energy for powering the devices 10, and data to be transmitted between the drive 8 and the devices 10.

Alternatively, the bus 11 may be dedicated to the transport of information, and not transport any energy.

Although FIG. 1 seems to show that the devices 10 are directly connected together, this is not the case in the real implementation: they are only connected together through the bus 11 to which they connect.

In the example described here, the bus 11 is made in the form of conducting wires. However, in other alternatives, it may be applied with a radio frequency link, an acoustic link, an inductive or other link.

As this will be seen subsequently, the bus 11 is asynchronous in the example described here, i.e. the bus 11 does not transport any synchronization signal (like a clock signal for example) for the devices 10.

Thus, the bus 11 is implanted in the body 4 in areas which are desirably driven, which may be close to the relevant nerves or muscles, and each device 10 is then connected to the bus 11. The bus 11 therefore represents a kind of spinal cord on which the devices 10 will be grafted, and each connected device 10 is a node of the bus 11.

The neural stimulation is entirely controlled by the drive 8. This approach represents a radical contrast with the approaches known to this day.

Indeed, the stimulations considered by the invention, for example those with a selective character, locally require an accuracy of the order of 1 microsecond, each device 10 having its own clock. The drift of the clock of the devices 10 is therefore present in this context, and its influence should not be neglected.

Consequently, any architecture centralized from a functional point of view, and distributed from an operational point of view as this is the case here, has been unrealistic up to today. Indeed, taking into account the consumption and therefore output constraints compatible with this context, synchronization was not possible at this time scale via a network.

Therefore the invention consisted in many improvements in each of the elements of the neural stimulation system 2 in order to allow operation in an operationally asynchronous but functionally synchronous mode.

By asynchronous operation, is meant the fact that the devices 10 are synchronized from a functional point of view but asynchronous from the point of view of their respective clocks.

This is notably obtained, as this will be seen in FIGS. 2 to 6, by means of the devices 10, which play a role of sophisticated actuators or sensors. Only the actuators will be discussed in detail, the statements remaining valid for the sensors.

Figure 2:
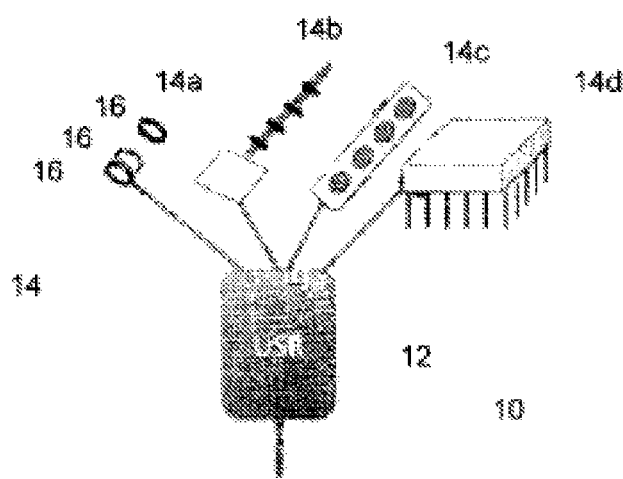
FIG. 2 illustrates a diagram of a device for controlling the human body of the system of FIG. 1.

FIG. 2 represents an exemplary neural stimulation device 10. As this may be seen in this figure, the device 10 comprises a control unit 12 and four electrodes 14 referenced as 14a, 14b, 14c and 14d, respectively.

As this will be seen in the following, the control unit 12 may provide both a stimulation role and a measurement role.

Each electrode 14 is laid out at a selected area of the nervous or muscular structure to be stimulated.

The four electrodes 14 depicted here illustrate in a non-exhaustive way various geometrical configurations of the contacts, associated with suitable mechanical structures: the electrode 14a is of the annular type, the electrode 14b of the intrafascicular type, the electrode 14c of the flat type and the electrode 14d of the matrix type.

In the example described here, the electrode 14a comprises three rings 16 each with four poles, which gives a total of 12 poles.

The electrode 14a may also include a more restricted number of rings, 3 for example, each with four poles, or another distribution of the number of rings and of poles per ring, notably within the scope of cochlear stimulation.

The total number of poles may vary with the retained configuration, and may be greater than or smaller than 12. This number typically varies from two in number for a bipolar or monopolar stimulation with a reference, to more than 24 for a cochlear application.

Generally, a device 10 includes a number of electrodes 14 comprised between 1 and 6, which are all driven by a single control unit 12, each electrode comprising between 1 and 12 poles.

Moreover, if in the application described here, the electrodes are neural, in other applications they may be epimysial, intramuscular, intracerebral, intrafascicular, cortical or other ones.

Figure 3:
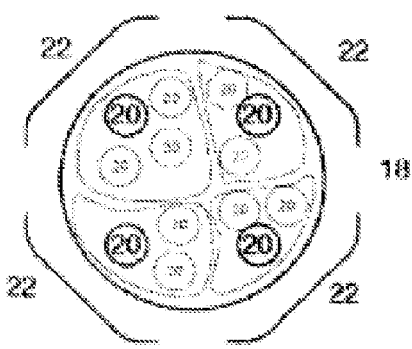
FIG. 3 illustrates a diagram of the distribution of the poles of one type of electrode of the device of FIG. 2.

FIG. 3 illustrates a schematic view of the arrangement of a ring of an electrode 14 around a nerve 18.

As this may be seen in this figure, the nerve 18 comprises four fascicles 19 each having several axons 20. The poles 22 of the ring 16 are regularly positioned around the nerve 18, so that each pole 22 is substantially facing a set of axons 20.

Thus, when the drive 8 sends to a device 10 a stimulation signal, the control unit 12 of this device 10 emits an electric stimulus at one or more poles 22 of a ring 16 of an electrode 14 of the device 10, and the subset of axons 20 facing this set of poles 22 is thereby stimulated.

Figure 4:
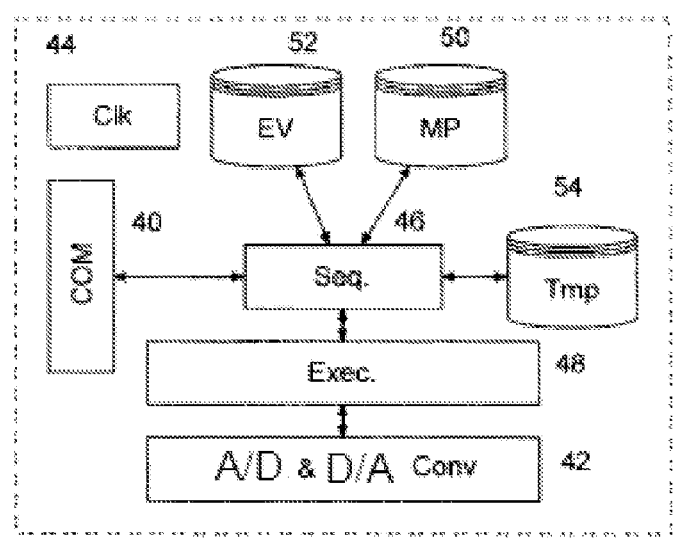
FIG. 4 illustrates a functional diagram of a portion of the device of FIG. 2.

FIG. 4 illustrates the architecture of a control unit 12. In the example described in this figure, the control unit 12 may handle one or more electrodes 14 either for stimulation or measurement purposes, via the analog/digital and digital/analog stages 42.

The control unit 12 comprises two main interfaces. The first interface, referenced as 40, is the interface for communicating with the bus 11. This interface 40 gives the possibility of receiving signals for powering and controlling the drive 8.

The second interface, reference 42, is the interface for communicating with the electrode 14 which is handled by the control unit 12. This interface 42 gives the possibility of controlling the stimulation of the axons 20 by the poles 22.

In the example described here, the interface 42 is integrated to a digital/analog converter to which it is assimilated, and the role of which will be explained further on.

The control unit 12 is a very low consumption circuit and clocked by a clock 44, the rate of which is of the order of 1 to 4 Mhz. This allows the control unit 12 to have an accuracy of the order of 1 microsecond.

One of the concepts implemented by the applicant for implementing the bus 11 asynchronously is the taking into account of the provided functions.

Indeed, in order to apply a stimulation of a muscle, the nerves which control its motor ability have to be stimulated with an accuracy of the order of 1 microsecond. As this was seen above, this corresponds to a clock frequency of the order of 1 megahertz.

Now, in order that the stimulation system be viable, the consumption of the devices 10 has to be controlled, which limits the rates of these devices to about a few megahertz.

Moreover, the asynchronous bus 11 does not allow synchronization of the devices 10, the clock of which is clocked at 1 megahertz, on a time scale of the order of 1 microsecond. In other words, the shift of the clocks of the devices 10 would be a problem if the devices 10 had to be totally synchronized by this means.

However, if it is necessary to synchronize the stimulations locally with an accuracy of the order of 1 microsecond, notably for considerations of selectivity of the stimulation, the characteristic time for synchronizing the muscular activities of the thereby stimulated muscles is of the order of a few milliseconds (ms).

Consequently, the applicant determined that there remains the possibility of asynchronously coordinating the devices 10 on a time scale greater than that of their own operation.

The control units 12 of the devices 10 then had to be designed so as to allow centralized control at the drive 8, of the distributed units formed by the devices 10, while ensuring time decoupling between the synchronization within each device 10 and the synchronization between the devices 10.

Figure 5:
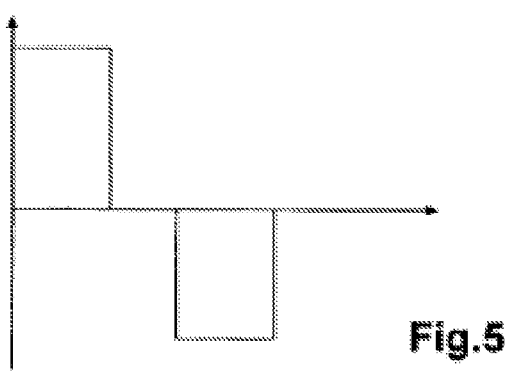
FIG. 5 illustrates an example of data stored in one of the elements of FIG. 4.

For this, the applicant designed an architecture in which each control unit 12 receives and executes instructions as microprograms which express a stimulation profile of the type of the one shown in FIG. 5. These microprograms are themselves ordered within the device 10, as a sequence of the type of the one illustrated in FIG. 6.

This principle may be applied both for measurement and for stimulation. Therefore, a microprogram may for example express an impedance measurement and a sequence may therefore contain an ordered series of measurements and of stimulations.

With this, it is possible to know the state of each of the devices 10, at the controller 8 with accuracy which limits the potential impact of the shift of their respective clocks with regard to muscle dynamics, i.e. the time separating the stimulus from the muscular response which it induces, and more generally the dynamics of the target structure, whether this be a sensorial or motor organ, or a neural structure.

The operating architecture of the control unit 12 is the following:

a sequencer 46 receives through the interface 40 requests from the drive 8, which are optionally accompanied by data. The optional data either correspond to microprograms or to multipolar configurations of the electrodes connected to the unit 12, or to the contents of the sequence applied by the sequencer. All these elements are described further on. The requests received by the sequencer 46 either correspond to driving orders (execute, stop, etc.) or to programming orders of the sequencer 46 (write the optional data and/or read data).

the sequencer 46 stores the received data in storage elements as described further on.

the sequencer 46 triggers, on request, the execution of microprograms on multipolar configurations. For this, it indicates the microprogram to be executed, to an executor 48, which is in the example described here, a specific microcontroller of the ASIP (Application Specific Instruction Set Processor) type, and the microcontroller 48 executes the series of instructions contained in the microprogram indicated by the sequencer and accordingly drives the digital/analog converter 42 which is connected to the electrodes. The microcontroller 48 also ensures the desired multipolar configuration on the corresponding electrodes.

A sequence defines a time window cut into intervals, inside which are designated stimulation programs to be executed on associated multipolar configurations in the intervals. The intervals may be parameterized in number and in duration.

In order to limit the amount of information in transit through the bus 11, the control unit 12 comprises a memory 50 for storing microprograms. In the example described here, the memory 50 stores eight distinct microprograms.

More specifically, the memory 50 comprises data which associate a microprogram identifier on the one hand and microprogram data on the other hand.

The microprogram data are series of instructions consisting of 24 bit words in the example described here, which correspond to various stimulation profiles. A stimulation profile describes the shape of the stimulus to be applied, with the different charging and discharging phases.

Table 1 of Appendix A illustrates a set of possible instructions for these words. Table 2 illustrates a microprogram which codes the stimulation profile illustrated in FIG. 5, where the ordinate axis designates the intensity of the stimulation and the abscissa axis designates the elapsed time relatively to the beginning of the interval. Table 3 illustrates another exemplary microprogram, the active phase of which is trapezoidal.

In these tables, the presence of modulation register data is noted. These registers are very advantageous. Indeed, the sequencer 46 maintains in the temporary memory 54, three modulation registers for the intensity I and three modulation registers for the duration T. More specifically, when the sequencer receives modulation data, it writes them directly into the relevant registers. When an instruction is executed and it comprises one or several references to addresses of these registers, the executor 48 takes this in account during its execution.

Thus, when a microprogram is written, the designer may provide the possibility of modulating the parameters of the instructions of this microprogram. Next, it is easy to modify the execution of each microprogram by acting on the value of the modulation register with which a given instruction is associated. This allows the practitioner to easily adapt the execution of a microprogram.

In the same way, the control unit 12, comprises a memory 52 for storing multipolar configurations of the electrodes 14. More specifically, each configuration indicates the poles of an electrode which are used. In the example described here, the memory 52 stores eight distinct configurations of electrodes per handled electrode. More specifically, the memory 52 comprises data which associate an electrode configuration identifier on the one hand and electrode configuration data on the other hand.

For the downstream stage considered as an example, the electrode configuration data are formed by a 72 bit word comprising configuration sub-words and ratio sub-words (current distribution among the active poles).

Each configuration sub-word will specify which pole is active and with which polarity, and each ratio sub-word will specify for each active pole what is the amount of current of the pulse which it will receive.

In the case of an electrode including 12 poles coupled via capacitors plus one non-coupled reference pole, the configuration of the electrode consists of defining how the current profile defined by the microprogram will be distributed over the whole of the poles of the electrode.

Therefore it is necessary to define for each pole:
 the polarity X (anode or cathode),
 the state Y of the pole (high impedance or active), and
 the ratio of current Z which crosses this pole.

The polarity may be coded on 1 bit (0 for anode and 1 for cathode), the state Y may be carried on 1 bit (0 for high impedance and 1 for active), and the current ratio Z may be coded on 4 bits (i.e. sixteen fractions of 0.0625 for each bit).

For example on 12 poles, distributed along 3 rings A1A2A3 of 4 poles P1P2P3P4, the configuration word is a sequence of 12 words of the XYZ type. The set XY forms for each pole the configuration sub-word, and Z forms the ratio sub-word, for example coded on 4 bits.

If it is for example intended to produce the equivalent of a conventional 3-pole electrode (a ring as a cathode in the centre and 2 anodes on the outside), we shall have:
 X=Anode Y=Active, Z=½ on all the poles of the rings A1 & A3, and
 X=Cathode Y=Active, Z=1 on all the poles of the ring A2.

This will give the following word:

| A1 | A1 | A1 | A1 | A2 | A2 | A2 | A2 | A3 | A3 | A3 | A3 |
|----|----|----|----|----|----|----|----|----|----|----|----|
| P1 | P2 | P3 | P4 | P1 | P2 | P3 | P4 | P1 | P2 | P3 | P4 |
| 01 | 01 | 01 | 01 | 11 | 11 | 11 | 11 | 01 | 01 | 01 | 01 |
| 1000 | 1000 | 1000 | 10001 | 1111 | 1111 | 1111 | 1111 | 1000 | 1000 | 1000 | 1000 |

Other elements may compose the configuration of an electrode and implicit configuration constraints may be expressed in the digital coding of this configuration (for example by using a reference).

In order to increase operational decentralization, the data stored in the memory 52 are reconfigurable. Indeed, although the indices of the memory 52 each designate in an absolute way a specific pole of an electrode, the drive 8 may send a request aiming at redefining these indices.

This allows the taking into account of possible displacements of the rings 16 around nerves 18 in the case of an annular electrode, or of other displacements for the other types of electrode.

Alternatively, the indices of the memory 52 may be relative, i.e. they may designate each pole with respect to a reference pole of the configuration. Thus, by loading a measurement device at the interface 42 (not shown for the sake of simplicity), the control unit 12 may reconfigure the electrode in the case of displacement of the latter.

It therefore appears that it is possible to drive the electrodes 14 per intervals by simply sending a triplet (interval reference in the window; electrode configuration identifier; microprogram identifier). Addressing of the triplet on the bus 11 allows designation of the device(s) 10 to which the triplet has to be applied.

Figure 6:
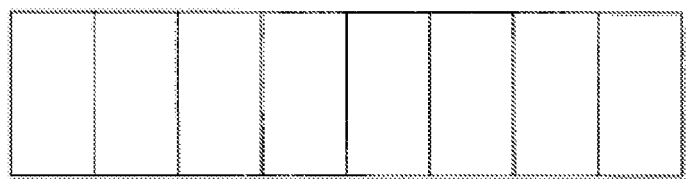
FIG. 6 illustrates an example of data stored in another of the elements of FIG. 4.

When the sequencer receives a control triplet, it stores the corresponding microprogram and the electrode configuration in the temporary memory 54. FIG. 6 illustrates an example of a window of intervals in the memory 54. And when the sequencer 46 receives a sequence execution order, it drives the microcontroller 48 according to the contents of the memory 54. When the control unit 12 handles several electrodes, the memories 50, 52 and 54 receive identifiers specific to each electrode, and the triplets are adapted accordingly.

With the foregoing, it therefore appears that the device 10 is designed so as to be totally remotely driven by the drive 8, with optimized power consumption and a minimum exchange of data between elements of the system.

For safety reasons, it is possible to reserve the last interval to the production of a passive discharge. Further, this last interval being of a duration which may be modified, it then allows fine adjustment of the repetition frequency of these stimulations.

Figure 7:
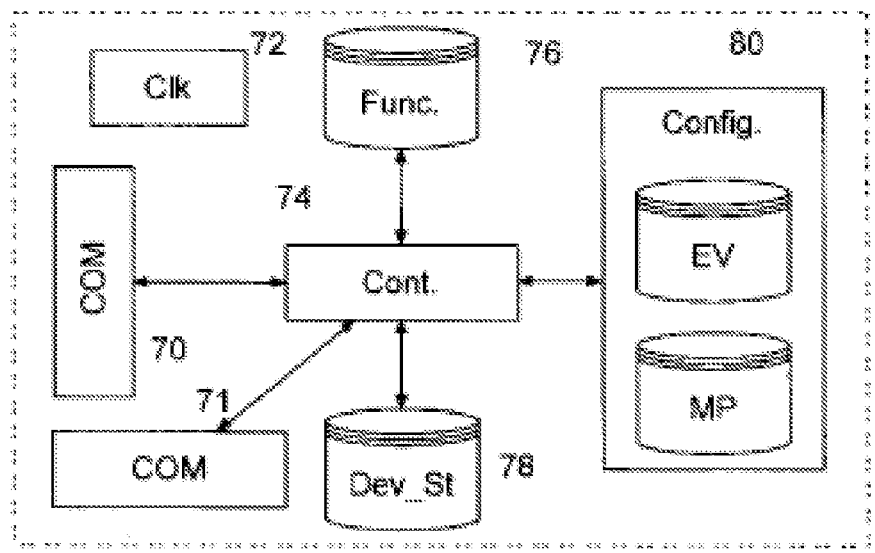
FIG. 7 illustrates a functional diagram of a neural stimulation drive of the device of FIG. 1.
Figure 8:
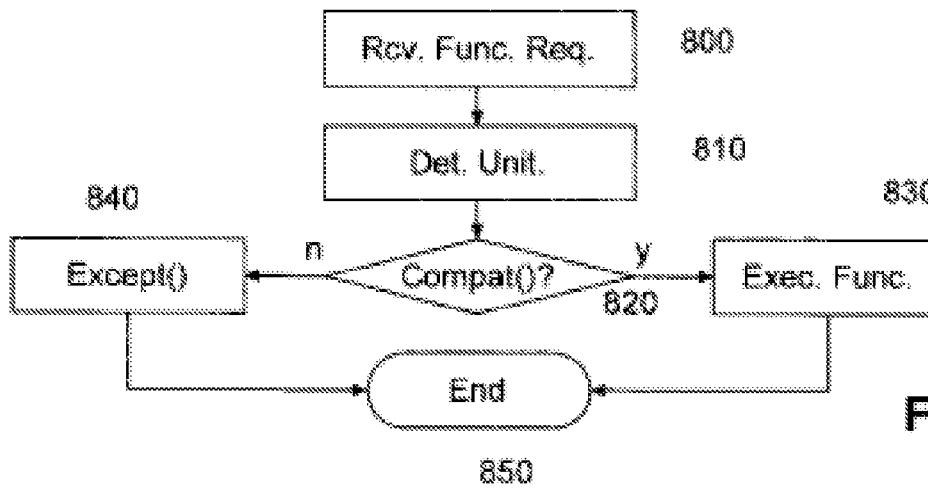
FIG. 8 illustrates an operating diagram of the drive of FIG. 7.

FIGS. 7 and 8 will give the possibility of showing the architecture of the drive 8 and the handling by the latter of the synchronization of the different devices 10.

As this may be seen in FIG. 7, the drive 8 comprises two communication interfaces 70 and 71, a clock 72, a controller 74 and memories 76, 78 and 80.

The communication interface 70 is connected to the bus 11 for transmitting the commands to various devices 10. The interface 71 ensures the wireless communication of the system with the external control 6, for example through an inductive link or through an RF link.

The clock 72 operates at about 12 MHz and ensures the coordinated performance of the various functions. The operating frequency of the clock may vary depending on the amount of information which the controller 74 has to communicate to the devices 10. The more the latter has to process "logic" instructions, i.e. of a high level and higher has to be the rate of the clock. Operation of the controller 74 will be explained with FIG. 8.

The memory 76 stores data which associate a motor function identifier on the one hand and motor function data on the other hand.

The motor function data comprise series, organized in a sequential and/or parallel way, of triplets (interval reference in the window; electrode configuration identifier; microprogram identifier) each designating an electrode of one or more given devices 10.

The notion of triplets as described here is not limiting. Indeed, the interval reference datum in the window may be implicit. The triplets therefore have to be considered as ordered pairs, the order of the pairs being explicit or implicit.

The set of these triplets defines coordinated activities (stimulation and/or measurement) which lead to performing a particular motor function.

For example, anode blocking may require a specific profile, the execution of which generates at least two adjacent stimulation square pulses on a set of electrodes consisting of a central cathode and of one or two optionally asymmetrical external anodes.

With this, it is for example possible to separately control the contraction of the striated sphincter of the urethra and the smooth muscle of the bladder (detrusor) innervated by a same set of nerves thereby ensuring more natural urination.

Another example consists of sequencing several triplets in order to obtain the stimulation of several muscles.

The question is to assign one electrode configuration per target muscle, i.e. a configuration of poles which may correspond to a different physical electrode or to a single electrode, the focal stimulation point of which is displaced.

This amounts to using one triplet per target muscle, each triplet potentially comprising the same profile, but distinct virtual electrodes sequenced in time.

It should be noted that locally, i.e. within a device 10, the sequencer may handle the activation of triplets organized as a sequence (series) and/or in parallel.

In the parallel case, the sequencer handles at the same time several windows consisting of intervals. The windows are then with identical characteristics, i.e. with a same number of intervals and of same durations.

The sequencer and the executor may have a similar architecture, i.e. if the sequencer accepts parallelism, then it will be advantageous if the executor also accepts this.

In this case, the sequencer and executor both operate according to a technique in which the sequencer determines the set of deadlines from the intervals in parallel at the relevant instant, and it drives the executor according to these deadlines.

If the sequencer does not accept parallelism, it is then preferable that the executor do not accept this either. The sequencer then drives the executor by asking it to activate the microprogram at the relevant instant.

Further, the sequencer may set into place the multipolar configuration before launching the executor, i.e. writing into the registers of the analog stage, during the available time between the end of the programmed activity in a current interval and the activation of a following interval.

With this it is possible to avoid any latency in the activation of the executor because of the setting into place of the configuration.

The memory 78 is a temporary memory which stores the "current" state of each window and of each of the electrodes of the devices 10.

Indeed, as the drive 8 is aware of which microprograms it has sent to which electrodes with their corresponding electrode configurations, it may store in the memory 78 a representation of the state of the latter for coordination purposes as discussed earlier.

The memory 78 also stores the present operating state of the stimulation system 2, i.e. the presently applied function(s), as well as a queue of the functions waiting to be applied.

With the queue, it is also possible to organize the ordered execution of the programmed functions on the one hand and of the sporadic functions on the other hand.

By programmed functions, are meant functions generally set into place by the practitioner, and which are exerted permanently, for example the anti-scar, anti-hyper-reflexia, anti-pain function, etc., . . . .

By sporadic functions are meant functions activated by the patient at a given instant, for example urination.

The memory 78 therefore allows organization of the execution of these functions.

The memory 80 is a configuration memory, which will store the whole of the memories 50 and 52 of each of the control units 12 of the devices 10. Thus, the drive 8 has a total view of the possible stimulations by the devices 10.

Further, the memory 80 may be used for reconfiguring certain devices 10. Indeed, a specific synchronization control between the memory 80 and the memories 50 and 52 of the devices 10 is provided.

FIG. 8 will now be described for explaining the operation of the controller 74.

The operation of the controller 74 may be seen as a permanently repeated loop. When the controller 74 receives an order for executing a function, transmitted by the external control 6 or a programmed function, a set of operations is launched.

The example of FIG. 8 starts at 800 upon receiving a function command from the external control 6.

Next, in an operation 810, the controller 74 calls the memory 76 with a function identifier drawn from the operation 800, and recovers the data relating to the performance of this function.

Next, in an operation 820, the controller 74 determines by means of a function Compat( ) whether this function command may be executed immediately.

The function Compat( ) may be based on calling the memory 78 in order to check which are the electrodes which are stimulated at this moment, and on calling compatibility data of this function with the functions presently implemented.

Thus there is a double check on the possibility of implementing the ordered function:

availability of the required electrodes (it is not possible to implement a new function if another function uses an electrode required for this implementation), and compatibility of the functions between them (it is not recommended to allow the possibility that the "getting up" and "urinating" functions be simultaneous).

Certain functions may be incompatible with each other while being individually activatable.

Thus, simultaneous execution of deambulation and of urination should not be authorized.

Conversely, it may prove to be necessary to activate several functions at the same time, such as generating a movement and inhibiting pain by neuro-modulation.

In the case when the system gives the possibility of evaluating certain parameters relating to the condition of the patient, the conditions determining authorization or the banning of the execution of certain functions may be dynamic.

For example, excessive tiredness may endanger an attempt to get up. Therefore this function should be blocked if a tired condition exceeding a given threshold is detected.

Other conditions may also play a role. Thus, constraints of technical nature such as the available energy or the failure of a subsystem, which in the absence of an emergency solution, may require the banning of the launching of a function, or even the interruption of execution of a current function.

If the function Compat( ) does not determine any problem upon executing the ordered function, then this function is controlled in an operation 830, i.e. the triplets defining it are transmitted in the required order to the various devices 10, or these triplets are simply activated if they have already been transmitted and stored in the memory 54 of the devices 12 involved in this function.

Otherwise, a function Except( ) is called in an operation 840. The function Except( ) has the role of determining whether the execution of the command received at 800 poses a major problem, which makes it incompatible with the existing queue, or not.

If this is the case, then a message indicating this impossibility of execution is sent to the external control 6 in order to inform the person. Otherwise, the function is placed in the queue of the memory 78.

Finally, the operation finishes at 850.

The implementation of diverse elements of this description, notably the different portions of the simulation unit 12 or the controller 8, may be carried out on components such as microcontrollers, microprocessors or digital signal processors (DSP).

The whole of the system was designed and prototyped for optimum utilization on digital architectures based on FGPA (Field Programmable Gate Array) components and their flash or OTP (One Time Programmable), ASIC (Application Specific Integrated Circuit) version.

APPENDIX A

TABLE 1 exemplary instruction set

| Name | Parameters | Comments |
|---|---|---|
| SIT | S | Sign |
|  | I | Intensity |
|  | RI, RT | I, T proportionality register address |
|  | T | Pulse duration (in µs) |
| RAMP | S | Sign |
|  | N | Number of steps |
|  | dI | I increment |
|  | dT | T increment (in µs) |
| DTL | End | End of program |
|  | N | Number of repetitions |

TABLE 1-continued exemplary instruction set

| Name | Parameters | Comments |
|---|---|---|
|  | Adr | Breakpoint address |
|  | T | Wait time before looping (in µs) |

TABLE 2

Example of a microprogram producing a biphasic rectangular stimulus, in which the active and discharge phases are of the same shape

| Name | Parameters | Meaning |
|---|---|---|
| SIT | +128 10 256 | Active square pulse variable in proportion to I, I = 128, T = 256 |
| DTL | 0 0 132 | High impedance phase of T-32 |
| SIT | −128 10 256 | Active discharge variable in proportion to T, I = 128, T = 256 |
| DTL | 1 0 0 64 | End of program after high impedance T = 64 |

APPENDIX A

Continued

TABLE 3

Another exemplary microprogram producing a trapezium-shape active phase and a rectangle-shaped active discharge

| Name | Parameters | Meaning |
|---|---|---|
| RAMP | +15 0 2 6 | Increasing ramp, 15 steps, I = 2, T = 6 |
| RAMP | −3 0 10 3 | Decreasing ramp, 3 steps, I = 10, T = 6 |
| SIT | −128 00 256 | Active discharge, I = 128, T = 256, not adjustable |
| DTL | 1 1 0 128 | End of program after 2 loops, T = 128 |

The invention claimed is:

1. A control system, implantable in a human body, comprising:
a drive comprising a drive clock; and
at least one control device connected in a wired network of the bus type, the control device comprising:
a control unit; and
at least one electrode, the control unit being connected to the electrode for controlling the electrode in at least one of stimulation and measurement,
the control unit including:
a timing clock,
a memory storing configuration data defined in order to allow configuration of the electrode in correspondence with identifiers;
a further memory storing program data describing a time profile in correspondence with identifiers,
an executor activatable to send to the electrode electric pulses corresponding to a given program according to a given electrode configuration, as a function of the timing clock, and
a sequencer laid out for receiving an ordered plurality of pairs each comprising an electrode configuration identifier and a program identifier, and for selectively activating the executor with electrode and program configuration pairs, designated by the pairs of identifiers received at an input, as a function of the order of receipt and the timing clock;

the drive being laid out in order to send, as a function of the drive clock, the plurality of pairs of identifiers to the sequencer.

2. The control system as recited in claim 1 wherein the at least one electrode includes 1 to 6 electrodes, each electrode comprising 1 to 12 poles, the electrode configuration data describing a state of activation of the poles of each electrode, a polarity and a current ratio.

3. The control system as recited in claim 1 wherein the program data comprise sign, intensity and duration data as well as modulation data associated with a memory for storing modulation value data.

4. The control system as recited in claim 1 further comprising at least one of an analog/digital converter and a digital/analog converter connected to the executor.

5. The control system as recited in claim 1 wherein the timing clock has an operating frequency above 1 MHz.

6. The system as recited in claim 1 wherein the drive further comprises:
 a drive memory for storing configuration data defined in order to allow configuration of the electrode in correspondence with identifiers, and program data describing a time profile in correspondence with the identifiers,
 a further drive memory for storing control data each designating at least one of the at least one device, which control data comprise an ordered plurality of pairs of identifiers each comprising an electrode configuration identifier and a program identifier, and
 a drive controller laid out for receiving control requests for the human body, and for selectively sending control data corresponding to at least one designated device of the at least one device, as a function of the state of the device.

7. The system as recited in claim 6 wherein the further memory stores a queue of control requests to be executed and a state of each device, and in which, before sending control data into the queue, the controller carries out a compatibility check with the state of each device.

8. The system as recited in claim 6 wherein the controller is laid out for sending modulation value data to the at least one device.

9. The system as recited in claim 1 wherein the clock of the drive has an operating frequency above 12 MHz.

10. The system as recited in claim 1 wherein the drive clock and the timing clock of the at least one device are asynchronous.

\* \* \* \* \*

UNITED STATES PATENT AND TRADEMARK OFFICE
CERTIFICATE OF CORRECTION

| | | |
|---|---|---|
| PATENT NO. | : 8,738,146 B2 | Page 1 of 1 |
| APPLICATION NO. | : 13/641366 | |
| DATED | : May 27, 2014 | |
| INVENTOR(S) | : David Guiraud et al. | |

It is certified that error appears in the above-identified patent and that said Letters Patent is hereby corrected as shown below:

On the Title Page, item (73), the Assignee section of the patent should read:

"Inria Institut National De Recherche En Informatique Et En Automatique,
Université Montpellier 2, Sciences et Techniques,
Obelia,
Centre National De La Recherche Scientifique (C.N.R.S)"

Instead of:

"Inria Institut National De Recherche En Informatique Et En Automatique,
Obelia,
Centre National De La Recherche Scientifique (C.N.R.S)"

Signed and Sealed this
Ninth Day of December, 2014

Michelle K. Lee
*Deputy Director of the United States Patent and Trademark Office*